United States Patent

Yamasaki et al.

Patent Number: 5,883,245
Date of Patent: Mar. 16, 1999

[54] DEODORIZER CONSISTING OF METALLOPHTHALOCYANINE AND PROCESS FOR PREPARING METALLOPHTHALOCYANINE

[75] Inventors: Yasuhiro Yamasaki, Neyagawa; Tatsuto Yamashita, Osaka, both of Japan

[73] Assignee: Orient Chemical Industries, Ltd., Osaka-fu, Japan

[21] Appl. No.: 942,358

[22] Filed: Oct. 2, 1997

[30] Foreign Application Priority Data

Oct. 2, 1996 [JP] Japan .................................. 8-261650
Aug. 11, 1997 [JP] Japan .................................. 9-216261

[51] Int. Cl.$^6$ ........................... C07D 478/22; C09B 47/00
[52] U.S. Cl. ...................... 540/140; 540/122; 540/129; 540/131; 540/139; 540/142; 540/144
[58] Field of Search ................... 540/122, 129, 540/131, 139, 140, 142, 144

[56] References Cited

U.S. PATENT DOCUMENTS 4,120,865 10/1978 Ward ........................... 260/314.5
5,569,758 10/1996 Klopp et al. .................. 540/122
5,618,930 4/1997 Kimura et al. ................ 540/143

FOREIGN PATENT DOCUMENTS 2104807 5/1987 WIPO .
3072501 3/1991 WIPO .

*Primary Examiner*—Mukund J. Shah
*Assistant Examiner*—Pavanaram K Sripada
*Attorney, Agent, or Firm*—Birch, Stewart, Kolasch & Birch, LLP

[57] ABSTRACT

The present invention provides a deodorizer consisting of the water-soluble metallophthalocyanine represented by the formula:

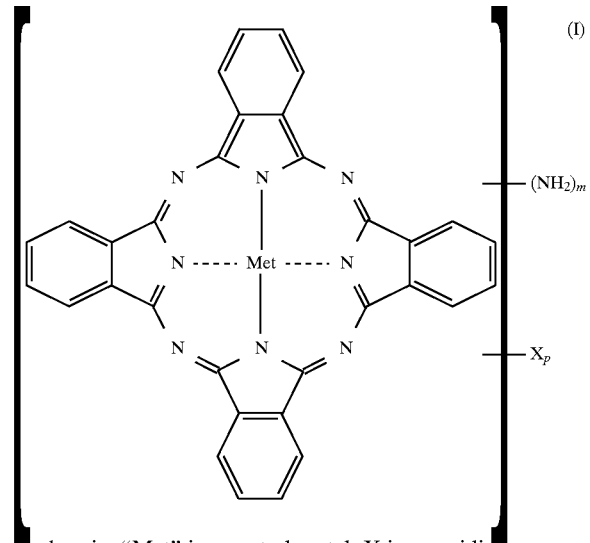

wherein, "Met" is a central metal, X is an acidic group or alkali metal salt thereof, m and p are respectively an integer of from 1 to 15, and m+p is not more than 16. The deodorizer shows excellent deodorizing ability for an aldehyde-origin odor.

15 Claims, 5 Drawing Sheets

DEODORIZER CONSISTING OF METALLOPHTHALOCYANINE AND PROCESS FOR PREPARING METALLOPHTHALOCYANINE

FIELD OF THE INVENTION

The present invention relates to metallophthalocyanine having deodorizing ability and a process for preparing metallophthalocyanine. Further, the present invention relates to a deodorizing material containing the above-described metallophthalocyanine as an effective component and a process for deodorizing an aldehyde-origin odor which is the main component of the odor of tobacco, and the like using the deodorizing material.

BACKGROUND OF THE INVENTION

It is conventionally known that phthalocyanine derivatives can be used as a deodorizer for deodorizing bad smell in living atmospheres. The deodorizing process by using phthalocyaninepolycarboxylic acid and phthalocyaninepolysulfonic acid, for example, is noticed as an artificial enzymatic oxidation deodorizing process, and is partially put into practice.

These phthalocyanine derivatives show excellent deodorizing ability for an ammonia odor (an amine-origin odor) and a mercaptan odor (a sulfur-origin odor), however, show insufficient deodorizing ability for an aldehyde-origin odor which is one of main components of a tobacco odor. It has been reported that ironphthalocyanine shows relatively good deodorizing ability. However, the deodorizing ability is insufficient for the aldehyde-origin odor, and is not practical as a deodorizer.

Further, ironphthalocyanine shows poor deodorizing ability for a sulfur-origin odor by comparison with cobaltphthalocyanine, and has poor stability in an alkali solution which is used for depositing it on a support. The deodorizing ability of the ironphthalocyanine, therefore, does not continue for a long period.

Japanese Patent Kokai Publication No. 63355/1981 discloses an ironphthalocyanine derivative, and the like obtained by the urea method, and it is described that the phthalocyanine derivative has deodorizing ability for an aldehyde-origin odor. However, the deodorizing ability thereof is not sufficient.

This kind of metallophthalocyanine is generally produced by the urea method (the Weilar method, or the phthalic anhydride liquid phase method, in other words), phthalonitrile method, and the like. The phthalonitrile method uses phthalonitriles as a raw material, and has the merits that reaction time is relatively short and yield is excellent. However, the phthalonitriles used as a raw material are expensive, and consequently the production cost becomes high. Further, it is pointed out that the phthalonitriles are toxic and, handling thereof requires attention from the view point of safety.

On the other hand, the urea method, particularly the phthalic anhydride liquid phase method is a method in which a phthalic acid derivative (for example, trimellitic anhydride), urea, a metallizing agent, and a catalyst are heated in a solvent. The raw materials used in the urea method are relatively inexpensive and have low toxicity, therefore, the urea method is low-cost and safe. However, a hydrophobic organic solvent such as nitrobenzene and trichlorobenzene is usually used as a solvent. It is therefore necessary to distill, remove, and recover the solvent from a reaction mixture after completion of the reaction.

When a solvent is distilled off from a reaction mixture, the reaction mixture is kept at high temperature under reduced pressure so that the mixture does not bump. This step takes a lot of time and labor, especially when the scale of the reaction becomes large. Therefore, the urea method has a demerit that the production process is complicated, especially upon mass production. Further, the hydrophobic organic solvents are harmful to the human body and to the environment, and handling thereof requires attention from the view point of safety.

The phthalic anhydride solid phase method does not use an organic solvent as a reaction solvent, therefore, it does not require labor for separating and recovering the organic solvent. However, the yield of this method is low, and the method is not suitable for mass production.

SUMMARY OF THE INVENTION

The present invention solves the above-described conventional problems, and the object thereof is to provide a deodorizer consisting of metallophthalocyanine, which shows excellent deodorizing ability for an aldehyde-origin odor, and a process for preparing the agent which enables high yield, low cost, safety and simplicity.

The present invention provides a deodorizer consisting of the water-soluble metallophthalocyanine represented by the formula:

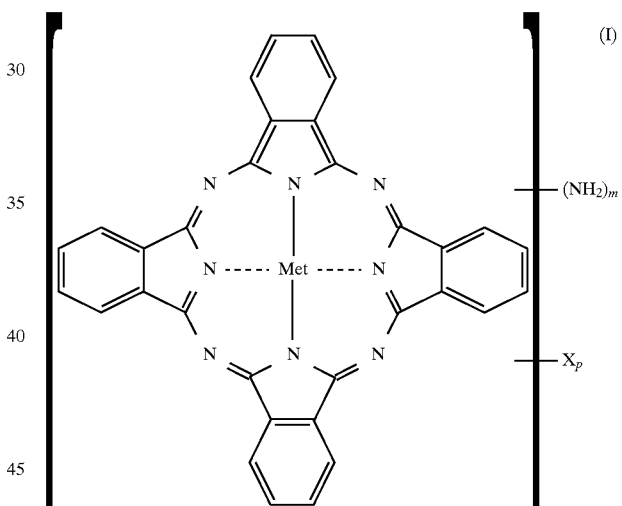

wherein, "Met" is a central metal, X is an acidic group or alkali metal salt thereof, m and p are respectively an integer of from 1 to 15, and m+p is not more than 16.

Further, the present invention provides a process for preparing the above-described deodorizer comprising the steps of:

heating a phthalic acid derivative having a nitro group, a phthalic acid derivative having an acidic group, urea, and metal halide, in polyethylene glycol dialkyl ether, in the presence of a condensation catalyst to obtain a metallophthalocyanine having a nitro group and an acidic group; and reducing the metallophthalocyanine having a nitro group and an acidic group.

The above-described water-soluble metallophthalocyanine is also useful as a functional colorant, and the like, and also can be used as a coloring agent for aqueous ink and color filter. However, the present inventors have newly found excellent deodorizing ability of this compound and have completed the present invention as a deodorizer.

The above-described process for preparing the deodorizer can be applied for preparing the metallophthalocyanine which can be produced by the urea method. Therefore, the present invention further provides a process for preparing metallophthalocyanine according to the urea method, in which polyethylene glycol dialkyl ether is used as a reaction solvent.

DETAILED DESCRIPTION OF THE INVENTION

Figure 1:
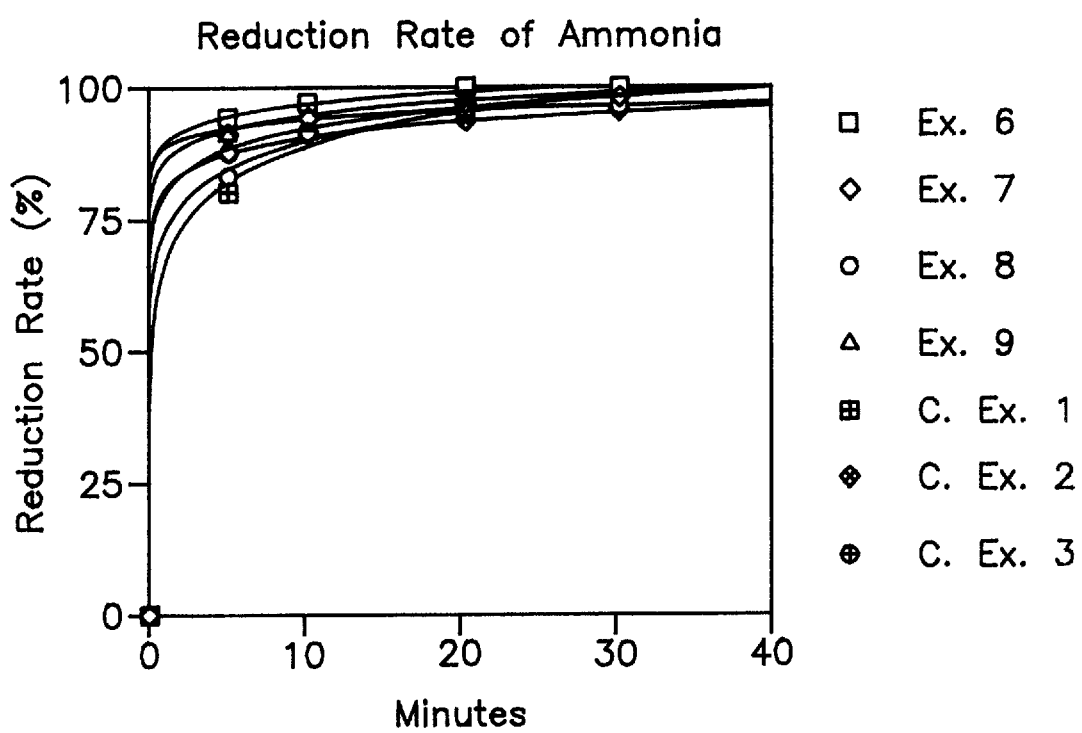
FIG. 1 is a graph which shows the deodorizing ability of the deodorizers in examples and comparative examples against ammonia.

In the deodorizer consisting of a water-soluble metallophthalocyanine of the present invention, the central metal is selected from lithium, potassium, calcium, barium, tin, chromium, iron (II or III), cobalt, nickel, manganese, osmium, titanium, beryllium, molybdenum, tungsten, copper and zinc. Manganese, cobalt, nickel and iron (II or III) are preferable.

The acidic group is selected from a carboxyl group, sulfonic acid group, phosphoric group, and the like. The carboxyl group and sulfonic acid group are preferred. The acidic group may also be a salt formed with alkali metal such as sodium, potassium and lithium.

The deodorizer consisting of a water-soluble metallophthalocyanine of the present invention has an amino group and acidic group as a substituent. The deodorizer of the present invention becomes water-soluble due to this structure. The water-soluble deodorizer has merits that it is easier treated in comparison with a water-insoluble deodorizer, and it can be carried by being dyed in an aqueous dye bath in general.

The number of each substituent can be appropriately controlled depending on abilities required for the water-soluble metallophthalocyanine, such as deodorizing ability, water-solubility, and the like.

The number of the amino group is from 1 to 15, generally from 1 to 7, and preferably from 1 to 3. The number of the acidic group is from 1 to 15, generally from 1 to 7, and preferably from 1 to 3. Further, the sum of the number of the amino group and the number of the acidic group is from 2 to 16, generally from 4 to 8, and preferably 4.

When the number of the amino group increases, basicity of the phthalocyanine increases, and consequently deodorizing ability for an aldehyde-origin odor may be expected. When the number of the acidic group increases, water-solubility of phthalocyanine increases, and consequently deodorizing ability for an amine-origin odor such as ammonia odor. Further when, the sum of the number of the amino group and the number of the acidic group increases, composite effect can be expected by two kinds of the substituent.

Examples of a combination of the substituents include, but are not limited to, 3 amino groups and 1 to 2 acidic groups; 2 amino groups and 2 to 4 acidic groups; 1 amino group and 3 to 6 acidic groups; 4 amino groups and 2 to 4 acidic groups, and the like. A mixture of a metallophthalocyanine having 1 to 4 amino groups and a metallophthalocyanine having 1 to 8 acidic groups also may be employed as a deodorizer of the present invention.

For example, when a carboxyl group or alkali metal salt thereof is used as the acidic group, examples of the combination include 3 amino groups and 1 carboxyl group; 2 amino groups and 2 carboxyl groups; 1 amino group and 3 carboxyl groups; 2 amino groups and 4 carboxyl groups; 2 amino groups and 6 carboxyl groups; 3 amino groups and 2 carboxyl groups; 4 amino groups and 4 carboxyl groups; and a mixture thereof. A water-soluble deodorizer can be provided, and bad smell in living atmosphere can be removed by using the deodorizer.

Further, when a sulfonic acid group or alkali metal salt thereof is for example used as the acidic group, examples of the combination include 1 amino group and 1 to 2 sulfonic acid groups; 2 amino groups and 1 to 4 sulfonic acid groups; 3 amino groups and 1 to 8 sulfonic acid groups; and a mixture thereof. A water-soluble deodorizer can be provided, and bad smell in living atmosphere can be removed by using the deodorizer.

The deodorizer consisting of a water-soluble metallophthalocyanine of the present invention can be deposited on various kinds of supports to provide a deodorizing material of the present invention. In this deodorizing material, an effective component which shows deodorizing ability is the water-soluble metallophthalocyanine. A method well known to those skilled in the art is used for depositing a water-soluble metallophthalocyanine to a support.

In particular, the deodorizer of the present invention is water-soluble, and a general aqueous dyeing method can be employed. By dissolving and dyeing the phthalocyanine in an aqueous medium, the phthalocyanine is uniformly deposited, and deodorizing ability thereof works well.

As the support, an inorganic or organic material is usually used. Examples thereof include inorganic materials such as silica gel and glass fiber; natural polymers such as cellulose, starch, gelatin, casein and guagum; synthetic polymers such as polyvinyl alcohol, poly(meth)acrylic acid, metal salt and alkyl ester thereof, poly(meth)acrylamide, poly(mono- or di-alkyl)amino(meth)acrylate, polyhydroxyalkyl (meth) acrylate, polyvinyl pyrrolidone, polyethylene oxide, polyvinyl sulfonic acid, metal salt thereof, polyvinyl ester, polystyrene, polyvinyl acetal, polyester, polyamide, amino resin, alkyd resin, and the like, and copolymers thereof;, and the like.

These materials are usually processed into a fibrous material and a granular material, and used as a support. Examples of the preferred support include a polymer powder or granules of a cellulose material such as modified cellulose, hydroxypropyl cellulose and carboxymethoxy cellulose, and a polymer powder or granules of acid-treated wool powder or granules. Examples of the method for depositing include a dyeing method, a setting method using a powder surface-modifying apparatus, and a coating method.

The deodorizing material obtained is effective for deodorizing bad smell in living atmosphere. Concretely, the obtained material shows excellent deodorizing ability against an aldehyde-origin odor in addition to an ammonia odor (an amine-origin odor) and a mercaptan odor (a sulfur-origin odor). This deodorizing material can be placed at the position where odor exists, for use.

The deodorizer consisting of a water-soluble metallophthalocyanine of the present invention can be prepared by synthesizing nitrophthalocyanine by a method usually used by those skilled in the art such as the urea method and phthalonitrile method, and by reducing the obtained nitrophthalocyanine to aminophthalocyanine. The preferable method for preparing the nitrophthalocyanine is the urea method. The reason for this is that this method has relatively short reaction time and gives excellent yield as described above.

According to the urea method (the phthalic anhydride liquid phase method), a metallophthalocyanine compound is generally prepared by heating a phthalic acid derivative such as phthalic anhydride and phthalimide, urea, and metal halide in an inert organic solvent in the presence of a condensation catalyst. This method is well known to the art, and specifically described in "Dye and Chemical", Vol. 23, No. 10, pp 213 to 215, (1978), "Recent technique for preparing phthalocyanine pigment [I]", and the like.

Examples of the phthalic acid derivative used as a raw material include trimellitic anhydride, pyromellitic dianhydride, 4-sulfophthalic acid, 4-sulfophthalic anhydride, 4-nitrophthalimide, 3-nitrophthalimide, 4-nitrophthalic anhydride, and the like.

Phthalic anhydride, alkyl-substituted phthalic acid, alkoxy-substituted phthalic acid, 4-chloro-5-nitrophthalimide, ammonium salt of phthalic acid, metal salt (Na salt, K salt) of phthalic acid, phthalate, phthalamide, phthalyl halogenate, phthalimide, o-cyanobenzoic acid, o-cyanobenzoate, and the like can also be used as the raw material.

Examples of the metal halide include copper (I) chloride, cobalt chloride (6 hydrate), iron (II, III) chloride, nickel chloride, aluminum chloride, and the like. Sulfate of polyvalent metal (for example, cobalt sulfate, copper sulfate, aluminum sulfate, chromium sulfate), nitrate (for example, copper (II) nitrate), phosphate of polyvalent metal, borate of polyvalent metal, or the like can also be used instead of the metal chloride.

Examples of the condensation catalyst include ammonium molybdate, molybdic acid, sodiummolybdate, silicomolybdic acid, phosphomolybdic acid, molybdenum oxide, ammoniumphosphomolybdate, phosphotungstomolybdic acid, molybdenum carbonyl, and the like. In general, ammonium molybdate is preferred.

As the inert organic solvent, a polyethylene glycol dialkyl ether is used. The polyethylene glycol dialkyl ether (polyglyme) represents the compound represented by the following formula (II):

$$R^1O(CH_2CH_2O)_nR^2 \qquad (II)$$

wherein, $R^1$ and $R^2$ independently represents an alkyl group having 1 to 8, preferably 1 to 4 carbon atoms, and n represents an integer of not less than 2, preferably from 2 to 10, more preferably from 3 to 5).

Specific examples thereof include diethylene glycol dimethyl ether (diglyme), triethylene glycol dimethyl ether (triglyme), tetraethylene glycol dimethyl ether (tetraglyme), polyethylene glycol dimethyl ether (a mixture of polyglymes in which n is 2 or 3 or more), diethylene glycol diethyl ether, triethylene glycol diethyl ether, tetraethylene glycol diethyl ether, diethylene glycol methyl ethyl ether, diethylene glycol dipropyl ether, diethylene glycol dibutyl ether, and the like. These can be used alone or in combination.

The polyethylene glycol dimethyl ether (generally referred to as polyglyme) represented by the formula (II) in which both $R^1$ and $R^2$ represent a methyl group is preferred. The particularly preferable examples include a polyglyme having a boiling point of not less than 180° C., for example, triglyme, tetraglyme, and the like.

The polyglyme has excellent miscibility with the phthalic acid derivative and the product, is inactive against the above-described reaction components such as the phthalocyanine derivatives, and the like, is water-miscible, and has no toxicity. By using the polyglyme as the inert organic solvent, the reactants does not flocculate, and the finely dispersed condition is maintained throughout the reaction. As a result, a uniform slurry reaction, and a condensation reaction at high temperature (from about 180° to about 200° C.) are possible. Furthermore, the polyglyme can be removed by washing with water and handling thereof is safe.

In the method of the present invention for preparing the deodorizer or metallophthalocyanine, the above-described reaction components are heated in an inert organic solvent to conduct a condensation reaction, by first. The urea is used in an amount of not less than 3 mol, preferably from 3 to 6 mol, the condensation catalyst is used in an amount of from 0.1 to 5% by mol, preferably from 0.1 to 1% by mol, and the metal halide is used in an amount of not less than ¼ mol, preferably from ¼ to ½, wherein the amount of the reactants is based on 1 mol of the phthalic acid derivative(s). The amount used of the inert organic solvent is not particularly limited to, but in case of the polyglyme, it is used in an amount of 2-fold or more, preferably from 4 to 6-fold, based on the weight of the phthalic acid derivative.

In particular, when a deodorizer of the present invention is prepared, a phthalic acid derivative having a nitro group such as 3-nitrophthalic acid, 4-nitrophthalic acid, triammonium sulfophthalate, 3-nitrophthalic anhydride, 4-nitrophthalic anhydride, 3-nitrophthalimide, 4-nitrophthalimide, 4-chloro-5-nitrophthalimide, and the like, together with a phthalic acid derivative having an acidic group such as trimellitic anhydride, pyromellitic anhydride, 3-sulfophthalic anhydride, 4-sulfophthalic anhydride, trimellitic acid, pyromellitic acid, 3-sulfophthalic acid, 4-sulfophthalic acid, and Na, K, and $NH_3$ salts thereof, and amide derivatives thereof, and the like, are used as the phthalic acid derivative. The both phthalic acid derivatives are used in suitable ratio as shown in the following examples for the condensation reaction.

The condensation reaction is kept at temperature of from 180° to 200° C. for 2 to 10 hours. In a preferred embodiment, the reaction is kept at temperature of from about 130° to 160° C. for 2 to 4 hours, or at temperature of from 180° to 200° C. for 4 hours or more, preferably for 4 to 10 hours.

After completion of the condensation reaction, the reaction mixture is cooled to about 100° C., hot water (about 80° C.) is added to the reaction mixture, and the mixture is stirred for 2 to 3 hours with refluxing. Then, filtered at high temperature and washing with hot water of the reaction mixture are repeated for several times to remove an inert organic solvent and an inorganic impurity. Since the organic solvent used in the present invention is water-soluble, the organic solvent can be easily separated from the reaction product by washing with water. The resulting solid is optionally washed with acetone or DMF, and dried to obtain metallophthalocyanine.

When the above-described reaction is conducted by using a phthalic acid derivative having a nitro group and a phthalic acid derivative having a carboxyl group or sulfonic acid group for preparing a deodorizer of the present invention, (nitrocarbamoilphthalocyaninato)metal or (nitrosulfamoilphthalocyaninato)metal are obtained. Metallophthalocyanine having an acid amide group is generally water-insoluble. However, the metallophthalocyanine can be made to water-soluble by hydrolyzing the acid amide group. That is, the acid amide group is converted to an acidic group, and water-soluble phthalocyanine having the acidic group (for example, (nitrocarboxyphtharocyaninato)metal or (nitrosulfophthalocyaninato)metal is water-soluble.

The method for hydrolyzing metallophthalocyanine having an acid amide group is well known to those skilled in the art. For example, after removal of an organic solvent in the condensation reaction, a wet cake of the obtained water-insoluble metallophthalocyanine is dispersed in a 5 to 30% aqueous alkali (for example, sodium hydroxide and potassium hydroxide) solution, and the mixture is stirred for 2 to 12 hours with refluxing. After cooling, a mineral acid (for example, concentrated hydrochloric acid, sulfuric acid) is added to obtain a slurry. The slurry is filtered, re-dispersed in hot water or water to remove salt components, inorganic and organic impurities, optionally washed with acetone or DMF, and dried, to obtain a water-soluble metallophthalocyanine.

When the condensation product is (nitrosulfophthalocyaninato)metal, alcohols (for example, methanol) are added into the reaction mixture, and the mixture is stirred for 2 to 3 hours with refluxing. Then, the reaction mixture is filtered at high temperature and washed with methanol to remove an inert organic solvent and an inorganic impurity, and the like. Solubility of (nitrosulfophthalocyaninato)metal into alcohols is poor, the (nitrosulfophthalocyaninato)metal can be made to a slurry, and it easily can be separated from the organic solvent used in the reaction.

The (nitrocarboxyphthalocyaninato)metal or (nitrosulfophthalocyaninato)metal (a nitrophthalocyanine derivative) is then reduced in liquid phase by using a reducing agent. Examples of the reducing agent include sodium sulfide, sodium polysulfide, a sulfur compound such as $Na_2S_2O_4$, hydrazine-raney nickel, Sn-HCl, Fe-HCl, $SnCl_2$-HCl, $Fe(OH)_2$, catalytic $H_2$, and the like. The reaction mixture is kept at temperature of not less than room temperature and from about 60° to 70° C. for 2 to 3 hours and 3 to 10 hours. When sodium sulfide 9 hydrate is used as a reducing agent, the amount used is preferably from about 5 to 10-fold mol as to a mono- or dinitrophtalocyanine derivative, and preferably from about 10 to 20-fold mol as to a tri or tetranitrophtalocyanine derivative.

It has been reported that a phthalic acid derivative is not suitable as a raw material for directly synthesizing a phthalocyanine pigment which is fine by comparison with phthalonitrile and 1,3-diiminoisoindolines since the phthalic acid derivative is not easily condensed in a hydrophilic organic solvent and scarcely forms metallophthalocyanine ("Dye and Chemical", Vol. 23, No. 11, pp 225 to 227, (1978), "Recent technique for preparing phthalocyanine pigment [II]"). Therefore, a hydrophilic organic solvent has been said unsuitable as an organic solvent used in the urea method.

For example, when an alcohol-based water-soluble solvent such as polyethylene glycol or ethylene glycol monoethyl ether is used as a solvent, intended metallophthalocyanine is scarcely obtained or the yield is low.

However, the present inventors have found that water-soluble metallophthalocyanine can be synthesized at high yield by the urea method when the specific hydrophilic organic solvent, that is, a polyethylene glycol dialkyl ether having high boiling point (for example, polyglyme), is used.

For example, when 4-nitrophthalimide (1) is used as a phthalic acid derivative having a nitro group, trimellitic anhydride (2) or pyromellitic dianhydride (3) is used as a phthalic acid derivative having an acidic group and these are mixed at a suitable ratio and subjected to a condensation reaction by the urea method in polyglyme, in the process of the present invention, there is obtained nitrometallophthalocyaninecarbamic acid. This compound is then hydrolyzed, and reduced in an aqueous medium by using a reducing agent such as sodium sulfide 9 hydrate to obtain water-soluble metallophthalocyanine (4) having a carboxyl group as an acidic group.

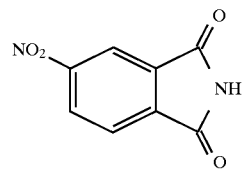

(1)

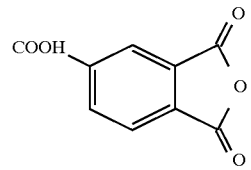

(2)

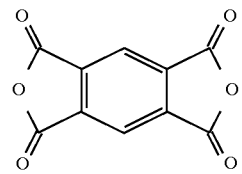

(3)

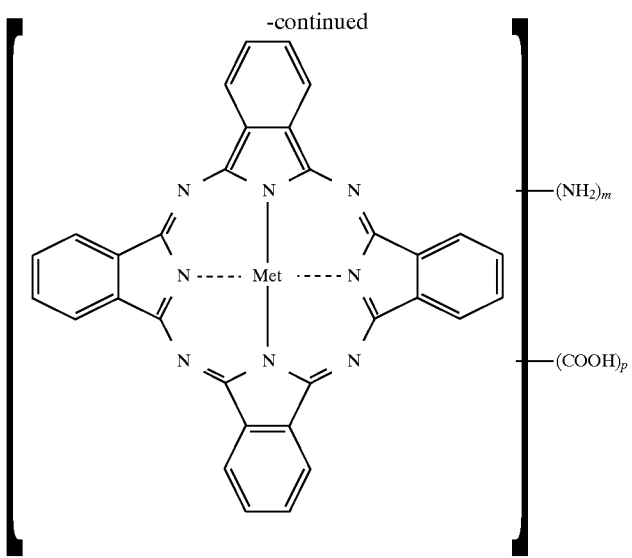

(4)

In the formula, "Met" is central metal, preferably cobalt or iron, and m and p is the same as defined above.

Further, for example, when 4-nitrophthalic anhydride (5) or 4-nitrophthalimide (1) is used as a phthalic acid derivative having a nitro group, 4-sodiosulfophthalic anhydride (6) is used as a phthalic acid derivative having an acidic group and these are mixed at a suitable ratio and subjected to a condensation reaction by the urea method in polyglyme, there is obtained (nitrosulfophthalocyaninato)metal. Next, this compound is reduced in an aqueous-phase by using a reducing agent such as sodium sulfide 9 hydrate to obtain a water-soluble metallophthalocyanine (7) having a sodium sulfonate group as an acidic group.

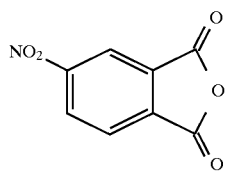

(5)

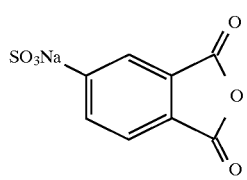

(6)

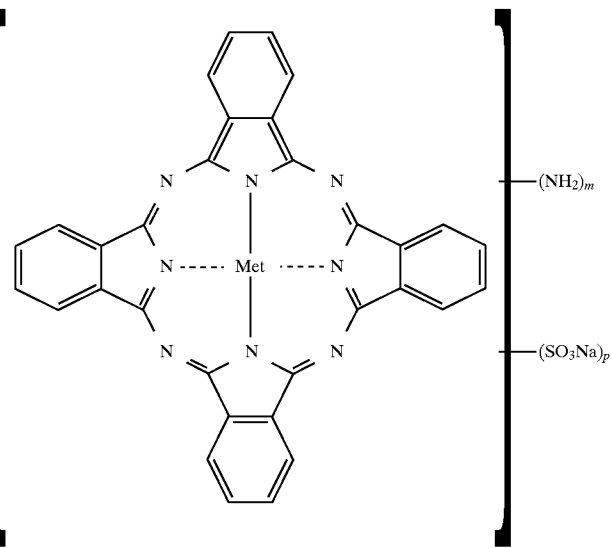

(7)

In the formula, "Met" is central metal, preferably cobalt or iron, and m and p is the same as defined above.

Metallophthalocyanine having an amino group as a substituent and metallophthalocyanine having an acidic group or alkali metal salt thereof as a substituent may be mixed, and the mixture may also be used as a deodorizer for effectively deodorizing an aldehyde-origin odor. However, the metallophthalocyanine having an amino group as a substituent is water-insoluble, and such a deodorizer cannot be dissolved in a aqueous solvent for use.

The number of an amino group of the metallophthalocyanine having an amino group as a substituent is from 1 to 16, generally from 4 to 8, preferably 4 or 8. The number of an acidic group or alkali metal salt thereof of the metallophthalocyanine having an acidic group or alkali metal salt thereof as a substituent is from 1 to 16, generally from 4 to 8, preferably 4 or 8.

The mixing ratio of the metallophthalocyanine having an amino group as a substituent and the metallophthalocyanine having an acidic group or alkali metal salt thereof as a substituent can be appropriately controlled depending on desired deodorizing ability and the number of substituents. For example, 10 to 90% by weight, preferably 20 to 80% by weight of the metallo- phthalocyanine having an amino group as a substituent and 10 to 90% by weight, preferably 20 to 80% by weight of the metallophthalocyanine having an acidic group or alkali metal salt thereof can be combined.

The metallophthalocyanine having an amino group as a substituent and the metallophthalocyanine having an acidic group or alkali metal salt thereof as a substituent used herein can be prepared by appropriately selecting and using phthalic acid derivatives as a raw material.

According to the process of the present invention, a metallophthalocyanine represented by the following formula (III) can be preferably prepared.

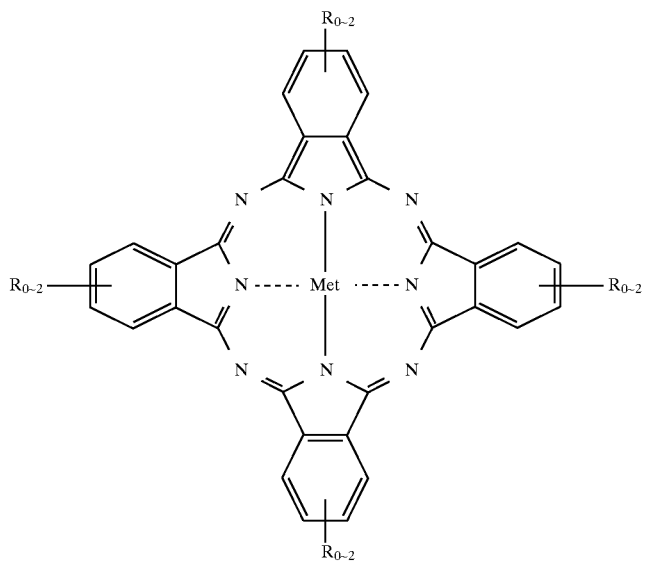

(III)

In the formula, R represents a nitro group, halogen atom, alkyl group, alkoxy group, amino group, carboxyl group, alkali metal salt of carboxyl group, and the like, "Met" represents polyvalent metal such as Cu, Co, Fe, Ni, Al, and Cr.

The metallophthalocyanine of the present invention thus obtained is useful as a deodorizer, photorecording material, photoconductive material, dye and pigment for coloring, functional colorant or the like.

For example, water-insoluble (tetranitrophthalocyaninato)copper is useful as a precursor of a functional phthalocyanine for various uses. Also, this nitrophthalocyanine can be reduced to obtain (tetraaminophthalocyaninato)copper. Further, a variety of (diazophthalocyaninato)copper derivatives can be obtained by diazotization of the amino compound.

The deodorizer consisting of a metallophthalocyanine of the present invention can deodorize bad smell consisting of an amine-origin odor such as an ammonia odor and of a sulfur-origin odor such as a mercaptan odor, and can show high deodorizing ability for an aldehyde-origin odor which is one of main components of a tobacco odor. It therefore removes a variety of bad smell in living atmosphere in various forms. The deodorizing ability of the deodorizer shows excellent durability since $\mu$-oxo dimerization or removal of the central metal in an alkali solution does not occur.

The process of the present invention for preparing a deodorizer or metallophthalocyanine has the following merits by comparison with the conventional urea method. The process shorten the production period and reduce the production cost, and is very advantageous when a scale of the production becomes large.

i) A solvent can be removed from a reaction product by simple procedure, that is, filtration and water-washing, and therefore no step is required for distilling the solvent under reduced pressure after completion of the reaction.

ii) Reaction and purification can be conducted on one step continuous procedure.

iii) There occur no problem that the reaction product adheres and sticks to the wall of a vessel, and becomes impossible to stir.

iv) A solvent has no toxicity and handling thereof is safe.

v) As a result, a metallophthalocyanine which has high purity and stable quality is obtained by simple and safe process in high yield.

EXAMPLES

The following examples further illustrate the present invention in detail but are not to be construed to limit the scope thereof.

Example 1

Synthesis of (aminotricarboxyphthalocyaninato)cobalt.

Into a 3000 ml four neck flask made of glass equipped with necessary equipment such as a stirrer, reflux condenser, and the like were charged 144.2 g of trimellitic anhydride, 48.1 g of 4-nitrophthalimide, 270 g of urea, 5.0 g of ammonium molybdate, 71.4 g of cobalt chloride 6 hydrate, and 1000 ml of triglyme. The resulting mixture was uniformly stirred for about 15 minutes at room temperature, then the mixture was stirred for 6 to 7 hours at temperature of from 125° to 130° C., and subsequently further stirred for 7 to 8 hours at temperature of from 180° to 190° C.

After cooling, 1500 ml of hot water of about 80° C. was gradually added to the reaction mixture, and further stirred for 3 hours with refluxing. After filtration at high temperature, the mixture was washed with 10 L of hot water. The wet cake was dispersed in 2.0 L of 20% aqueous potassium hydroxide solution, and hydrolyzed for 12 hours with refluxing. About 780 ml of concentrated hydrochloric acid was added with maintaining the temperature not more than 20° C. in an ice bath to regulate pH thereof to 1 to 2, then the mixture was stirred for about one hour at room temperature. After filtration, the resulted wet cake was desalted by washing with 10 L of water, then dried to obtain 97.4 g of (nitrotricarboxyphthalocyaninato)cobalt.

85.0 g of the resulted powder was dispersed in 500 ml of water, and 66.0 g of sodium sulfide 9 hydrate was gradually added. The mixture was heated with stirring for 2 hours at temperature of 30° C. and further for 5 hours at temperature of from 60° to 70° C. The mixture was cooled to room temperature, then, to this was added 2500 ml of water, pH thereof was regulated to about 4.0 with hydrochloric acid, further stirred for one hour, filtered, subsequently washed with about 15 L of water, dried, to obtain 90.3 g of a blue solid. The structure of the resulted compound is shown below.

and the like were charged 96.1 g of trimellitic anhydride, 96.1 g of 4-nitrophthalimide, 270 g of urea, 5.0 g of ammoniummolybdate, 71.4 g of cobalt chloride 6 hydrate, and 1000 ml of triglyme. The resulting mixture was uniformly stirred for about 15 minutes at room temperature, then the mixture was stirred for 6 to 7 hours at temperature of from 125° to 130° C., and subsequently further stirred for 7 to 8 hours at temperature of from 180° to 190° C.

After cooling, 1500 ml of hot water of about 80° C. was gradually added to the reaction mixture, and further stirred for 3 hours with refluxing. After filtration at high temperature, the mixture was washed with 10 L of hot water. The wet cake was dispersed in 2.0 L of 20% aqueous potassium hydroxide solution, and hydrolyzed for 12 hours with refluxing. About 780 ml of concentrated hydrochloric acid was added with maintaining the temperature not more than 20° C. in an ice bath to regulate pH thereof to 1 to 2, then the mixture was stirred for about one hour at room temperature. After filtration, the resulted wet cake was desalted by washing with 10 L of water, then dried to obtain 130.9 g of (dinitrodicarboxyphthalocyaninato) cobalt.

75.0 g of the resulted powder was dispersed in 500 ml of water, and 125.0 g of sodium sulfide 9 hydrate was gradually added. The mixture was heated with stirring for 2 hours at temperature of 30° C. and further for 5 hours at temperature of from 60° to 70° C. The mixture was cooled to room temperature, then, to this was added 2500 ml of water, pH thereof was regulated to about 4.0 with hydrochloric acid, further stirred for one hour, filtered, subsequently washed with about 15 L of water, dried, to obtain 74.6 g of a blue solid. The structure of the resulted compound is shown below.

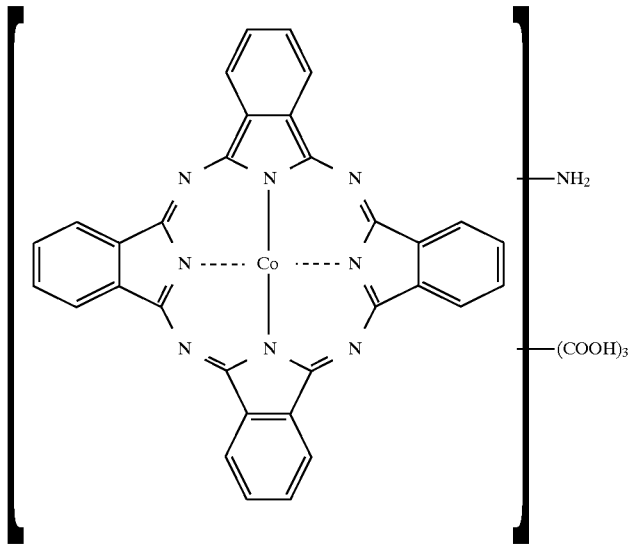

Example 2

Synthesis of (diaminodicarboxyphthalocyaninato)cobalt.

Into a 3000 ml four neck flask made of glass equipped with necessary equipment such as a stirrer, reflux condenser,

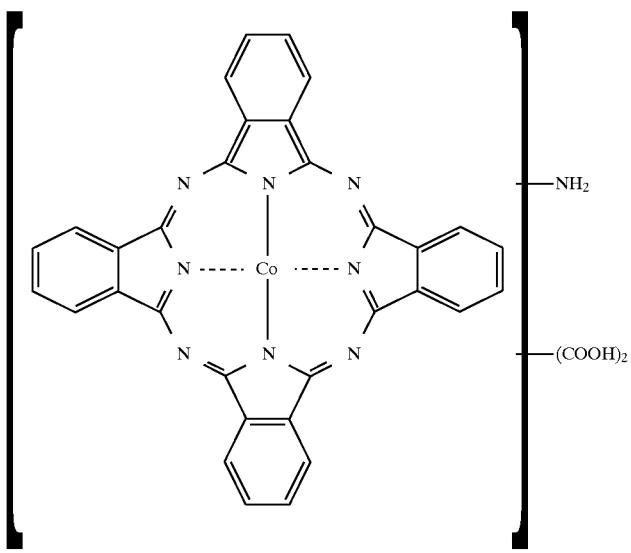

Example 3
Synthesis of (triaminocarboxyphthalocyaninato)cobalt.

Into a 3000 ml four neck flask made of glass equipped with necessary equipment such as a stirrer, reflux condenser, and the like were charged 48.1 g of trimellitic anhydride, 144.2 g of 4-nitrophthalimide, 270 g of urea, 5 g of ammoniummolybdate, 71.4 g of cobalt chloride 6 hydrate, and 1000 ml of triglyme. The resulting mixture was uniformly stirred for about 15 minutes at room temperature, then the mixture was stirred for 6 to 7 hours at temperature of from 125° to 130° C., and subsequently further stirred for 7 to 8 hours at temperature of from 180° to 190° C.

After cooling, 1500 g of hot water of about 80° C. was gradually added to the reaction mixture, and further stirred for 3 hours with refluxing. After filtration at high temperature, the mixture was washed with 10 L of hot water. The wet cake was dispersed in 2.0 L of 20% aqueous potassium hydroxide solution, and hydrolyzed for 12 hours with refluxing. About 780 ml of concentrated hydrochloric acid was added with maintaining the temperature not more than 20° C. in an ice bath to regulate pH thereof to 1 to 2, then the mixture was stirred for about one hour at room temperature. After filtration, the resulted wet cake was desalted by washing with 10 L of water, then dried to obtain 156.0 g of (trinitrocarboxyphthalocyaninato)cobalt.

112.5 g of the resulted powder was dispersed in 500 ml of water, and 270.0 g of sodium sulfide 9 hydrate was gradually added. The mixture was heated with stirring for 2 hours at temperature of 30° C. and further for 5 hours at temperature of from 60° to 70° C. The mixture was cooled to room temperature, then, to this was added 2500 ml of water, pH thereof was regulated to 5.5 to 6.0 until the solubility of the product reaches minimum value with hydrochloric acid and an aqueous sodium hydroxide solution, filtered, subsequently washed with about 15 L of water, dried, to obtain 122.9 g of a blue solid. The structure of the resulted compound is shown below.

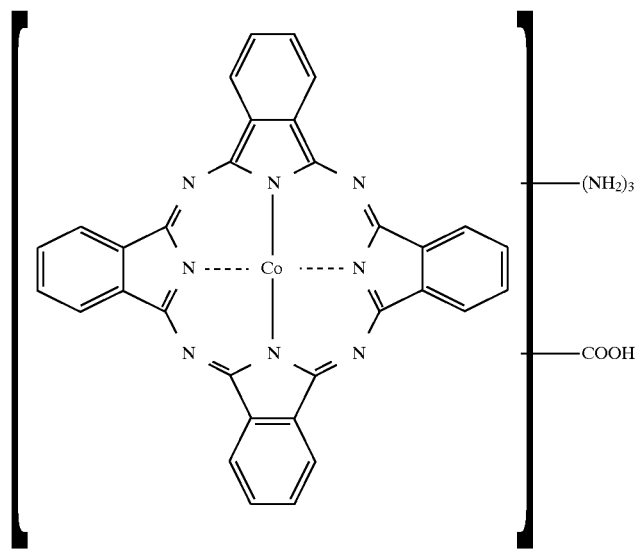

Example 4

Synthesis of (diaminodicarboxyphthalocyaninato)cobalt.

In to a 3000 ml four neck flask made of glass equipped with necessary equipment such as a stirrer, reflux condenser, and the like were charged 96.1 g of trimellitic anhydride, 96.1 g of 4-nitrophthalimide, 270 g of urea, 5.0 g of ammoniummolybdate, 48.7 g of anhydrous iron (I) chloride, and 1000 ml of tetraglyme. The resulting mixture was uniformly stirred for about 15 minutes at room temperature, then the mixture was stirred for 6 to 7 hours at temperature of from 125° to 130° C., and subsequently further stirred for 7 to 8 hours at temperature of from 180° to 190° C.

After cooling, 1500 ml of hot water of about 80° C. was gradually added to the reaction mixture, and further stirred for 3 hours with refluxing. After filtration at high temperature, the mixture was washed with 10 L of hot water. The wet cake was dispersed in 2.0 L of 20% aqueous potassium hydroxide solution, and hydrolyzed for 12 hours with refluxing. About 740 ml of concentrated hydrochloric acid was added with maintaining the temperature not more than 20° C. in an ice bath to regulate pH thereof to 1 to 2, then the mixture was stirred for about one hour at room temperature. After filtration, the resulted wet cake was desalted by washing with 10 L of water, then dried to obtain 93.8 g of (dinitrodicarboxyphthalocyaninato)iron (III).

14.9 g of the resulted powder was dispersed in 500 ml of water, and 125.0 g of sodium sulfide 9 hydrate was gradually added. The mixture was heated with stirring for 2 hours at temperature of 30° C. and further for 5 hours at temperature of from 60° to 70° C. The mixture was cooled to room temperature, then, to this was added 500 ml of water, pH thereof was regulated to about 4.0 with hydrochloric acid, further stirred for one hour, filtered, subsequently washed with about 15 L of water, dried, to obtain 14.8 g of a blue solid. The structure of the resulted compound is shown below.

Example 5

Synthesis of sodium salt of (diaminodisulfonicphthalocyaninato)cobalt.

Into a 3000 ml four neck flask made of glass equipped with necessary equipment such as a stirrer, reflux condenser, and the like were charged 96.1 g of sodium 4-sulfonate phthalic anhydride, 96.1 g of 4-nitrophthalimide, 270 g of urea, 5.0 g of ammonium molybdate, 71.4 g of cobalt chloride 6 hydrate, and 1000 ml of triglyme. The resulting mixture was uniformly stirred for about 15 minutes at room temperature, then the mixture was stirred for 6 to 7 hours at temperature of from 125° to 130° C., and subsequently further stirred for 7 to 8 hours at temperature of from 180° to 190° C.

After cooling, 1500 g of methanol was gradually added to the reaction mixture, and further stirred for 3 hours with refluxing. After filtration at high temperature, the mixture was washed with 10 L of dropping methanol.

14.9 g of the resulted powder was dispersed in 500 ml of water, and 125.0 g of sodium sulfide 9 hydrate was gradually added. The mixture was heated with stirring for 2 hours at temperature of 30° C. and further for 5 hours at temperature of from 60° to 70° C. The mixture was cooled to room temperature, then, to this was added 500 ml of water, pH thereof was regulated to about 4.0 with hydrochloric acid, further stirred for one hour, filtered, subsequently washed with about 15 L of dropping methanol, dried, to obtain 14.8 g of a blue solid. The structure of the resulted compound is shown below.

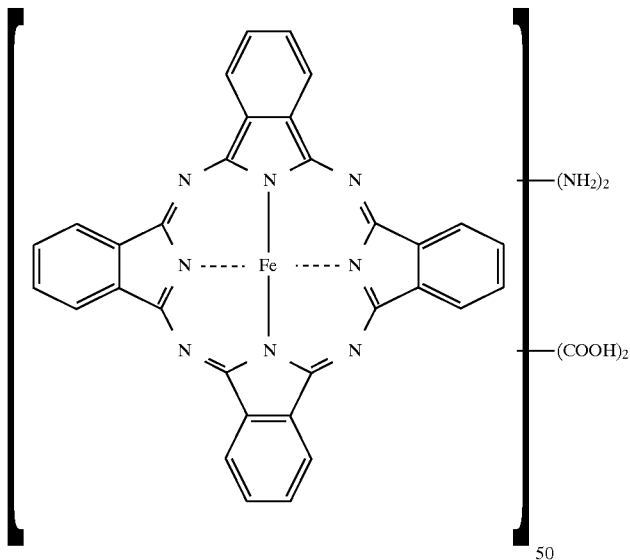

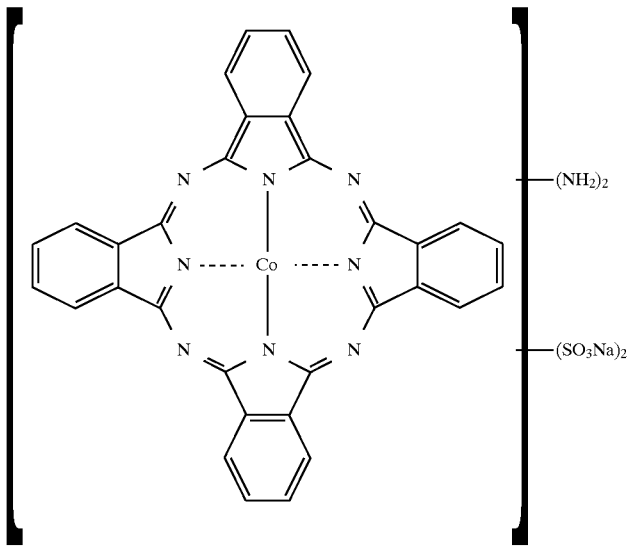

Example 6

0.1 g of (aminotricarboxyphthalocyaninate)cobalt synthesized in Example 1 (CPAC-1,3) was uniformly spread on a 10×10 cm² filter paper (Toyo filter paper No. 2) to prepare a deodorizing material. Three pieces of this deodorizing material were prepared, and respectively placed in three 3 L tetrabags. 30 ppm of ammonia, 5.0 ppm of hydrogen sulfide and 100 ppm of acetaldehyde were then charged into each tetrabag.

Figure 2:
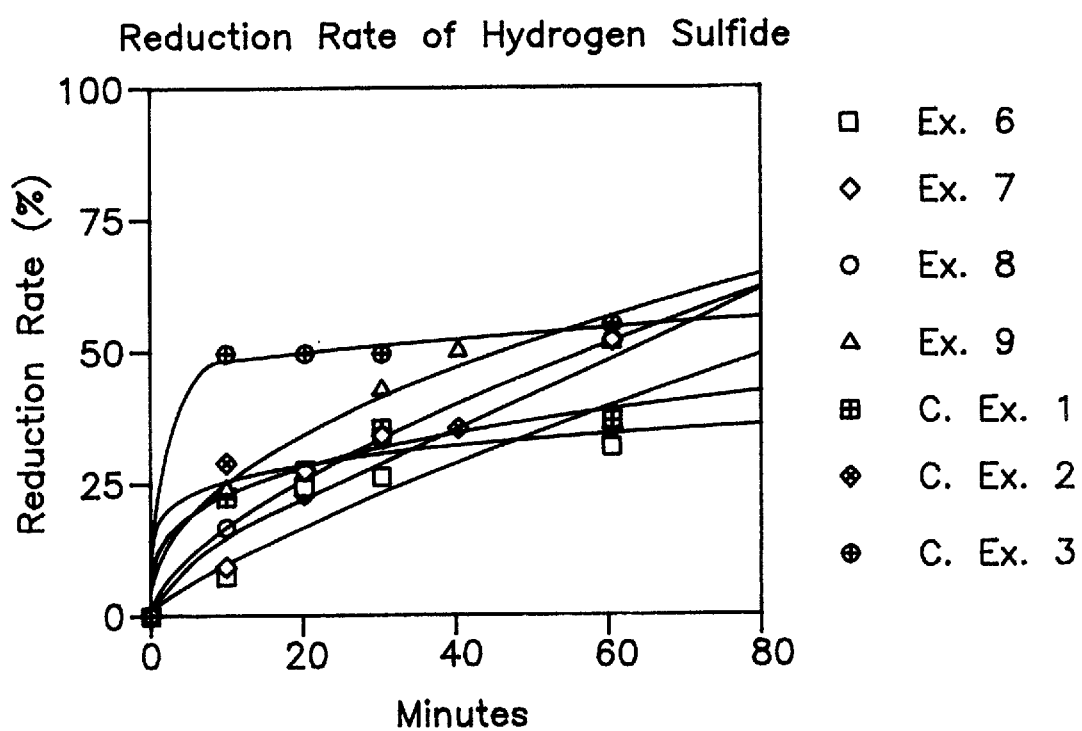
FIG. 2 is a graph which shows the deodorizing ability of the deodorizers in examples and comparative examples against hydrogen sulfide.

The amounts of ammonia, hydrogen sulfide and acetaldehyde remaining were measured by the detecting tube method with the lapse of time. The reduction rates of the substances were respectively shown in FIGS. 1, 2 and 3.

Example 7

The same procedure as in Example 6 was conducted except that (diaminodicarboxyphthalocyaninato)cobalt (CPAC-2,2) synthesized in Example 2 was used as a deodorizer, instead of CPAC-1,3.

Example 8

The same procedure as in Example 6 was conducted except that (triaminocarboxyphthalocyaninato)cobalt (CPAC-3,1) synthesized in Example 3 was used as a deodorizer, instead of CPAC-1,3.

Example 9

The same procedure as in Example 6 was conducted except that (diaminodicarboxyphthalocyaninato)iron (FPAC-2,2) synthesized in Example 4 was used as a deodorizer, instead of CPAC-1,3.

Example 10

Synthesis of (tetraaminophthalocyaninato)copper.

Into a 5000 ml four neck flask made of glass equipped with necessary equipment such as a stirrer, reflux condenser, and the like were charged 500 g of 4-nitrophthalimide, 660 g of urea, 20 g of ammonium molybdate, 70 g of copper (I) chloride and 2500 ml of triglyme. The resulting mixture was stirred for 1 to 2 hours at temperature of from 125° to 135° C., and subsequently further stirred for 6 hours at temperature of from 160° to 180° C.

After cooling, 2500 g of hot water of about 80° C. was gradually added to the flask, and further stirred for 3 hours with refluxing. The reaction product was filtered at high temperature, and washed with 10 L of hot water. The filtered material was dried to obtain 460 g of (tetraaminophthalocyaninato)copper.

10.4 g of the resulted (tetraaminophthalocyaninato) copper was dispersed in 300 ml of water, and 49 g of sodium sulfide 9 hydrate was gradually added. The mixture was heated with stirring for 3 hours at temperature of 30° C. and further for 5 hours at temperature of from 60° to 70° C. The mixture was cooled to room temperature, then, to this was added 2500 ml of water, pH thereof was regulated to about 4.0 with hydrochloric acid.

This reaction product was further stirred for one hour, filtered, subsequently washed with about 15 L of water. The filtered material was dried to obtain 7.6 g of (tetraaminophthalocyaninato)copper.

Synthesis of (tetracarboxyphthalocyaninato)cobalt.

Into a 10000 ml four neck flask made of glass equipped with necessary equipment such as a stirrer, reflux condenser, and the like were charged 1152 g of trimellitic anhydride, 1800 g of urea, 10 g of ammonium molybdate, 360 g of cobalt chloride 6 hydrate and 3000 g of triglyme. The resulting mixture was stirred for 1 hour at temperature of 130° C., and subsequently stirred for 4 hours at temperature of 200° C.

The mixture was cooled to about 100° C., 5000 g of hot water of about 80° C. was gradually added to the reaction mixture, and further stirred for 2 to 3 hours with refluxing. After filtration at high temperature, the mixture was washed with 30 L of hot water. Then, the resulted wet cake was dropped into 6000 parts of 20 to 30% aqueous potassium hydroxide solution, and the mixture was stirred for 12 hours with refluxing. The reaction mixture was cooled using a water/ice bath, 4130 g of concentrated hydrochloric acid was added dropwise so that the temperature did not exceed 30° C., then the mixture was further stirred for one hour. The resulted slurry was filtered, and was desalted by washing with 80 to 100 L of water. The filtered material was dried to obtain 693.4 g of (tetracarboxyphthalocyaninato)cobalt.

Figure 3:
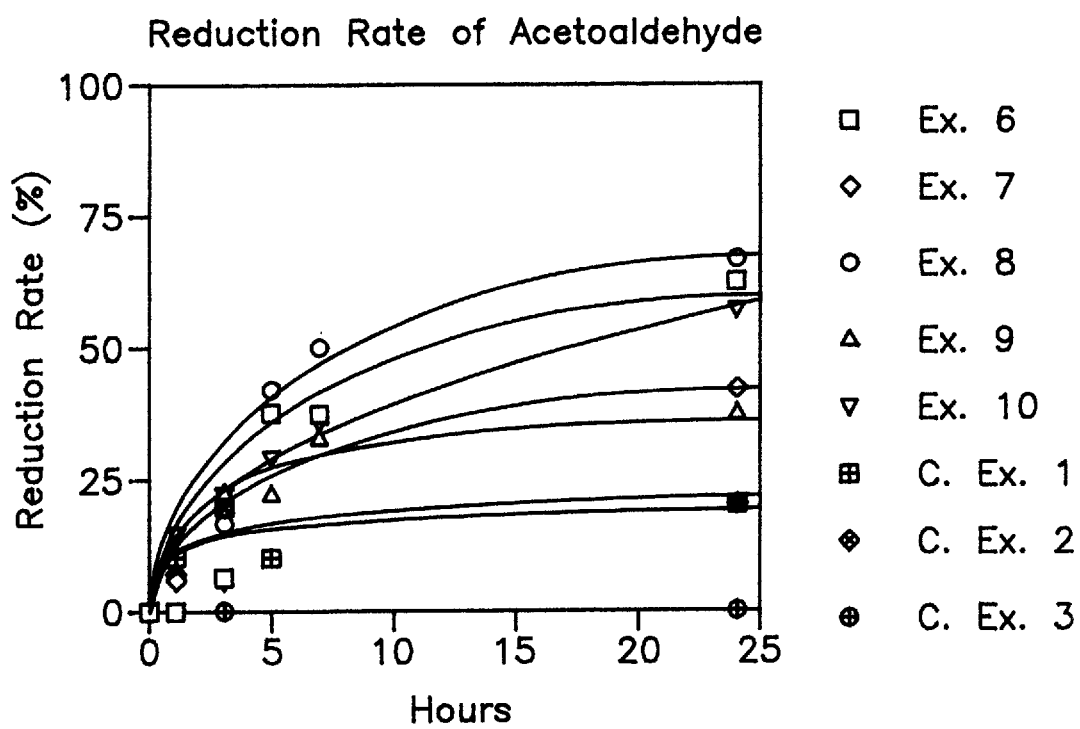
FIG. 3 is a graph which shows the deodorizing ability of the deodorizers in examples and comparative examples against acetaldehyde.

0.1 g of a deodorizer was obtained by mixing 0.05 g of (tetraaminophthalocyaninato)copper and 0.05 g of (tetracarboxyphthalocyaninato)cobalt. A deodorizing test was conducted for an aldehyde-origin odor in the same manner as in Example 6 except that the deodorizer herein obtained was used. The results are shown in FIG. 3.

Comparative Example 1

The same procedure as in Example 6 was conducted except that (tetracarboxyphthalocyaninato)iron (FPC-4)

synthesized according to the method described in example 14 was used as a deodorizer, instead of CPAC-1,3.

Comparative Example 2

The same procedure as in Example 6 was conducted except that (octacarboxyphthalocyaninato)iron (FPC-8) synthesized according to the method described in example 15 was used as a deodorizer, instead of CPAC-1,3.

Comparative Example 3

The same procedure as in Example 6 was conducted except that (tetracarboxyphthalocyaninato)cobalt (CPC-4) synthesized according to the method described in example 13 was used as a deodorizer, instead of CPAC-1,3.

Example 11

The catalytic activation ability was measured as to the deodorizers synthesized in Examples 1 to 4 of the present invention and (octacarboxyphthalocyaninato)iron (FPC-8) synthesized separately, based on the consumption-velocity of dissolved oxygen by an oxidation reaction of 1-mercapto-2-ethanol.

Measuring Method

A dissolved oxygen content measuring apparatus, recording apparatus, and the like were set, distilled water was charged into a vessel equipped with a jacket, and the saturated dissolved oxygen content was measured, then, an aqueous phthalocyanine solution separately prepared of which concentration was known was introduced in prescribed amount. Then, a reducing curve of saturated dissolved oxygen content was recorded with the lapse of time. The catalytic activation ratio was calculated from the speed ratio obtained from the curve. The results are shown in Table 1.

TABLE 1

|  | Compound | Catalytic activation ratio |
| --- | --- | --- |
| Example 1 | CPAC-1, 3 | 24.3 |
| Example 2 | CPAC-2, 2 | 22.6 |
| Example 3 | CPAC-3, 1 | 22.1 |
| Example 4 | FPAC-2, 2 | 1.1 |
| Control Example | FPC-8 | 1.0 |

Example 12
Synthesis of (tetranitrophthalocyaninato)copper.

Into a 5000 ml four neck flask made of glass equipped with necessary equipment such as a stirrer, reflux condenser, and the like were charged 500 g of 4-nitrophthalimide, 660 g of urea, 20 g of ammonium molybdate, 70 g of copper (I) chloride and 2500 g of triglyme. The resulting mixture was stirred for 1 to 2 hours at temperature of 130° C., and subsequently stirred for 2 hours at temperature of 160° C., then, further stirred for 4 hours at temperature of 180° C.

After cooling to about 100° C., 2500 g of hot water of about 80° C. was gradually added, and further stirred for 2 to 3 hours with refluxing. The reaction product was filtered at high temperature, then washed with 10 L of hot water. The product was dried to obtain 460 g of an intended compound at a yield of 93.6%. The result of the elemental analysis of this compound and the yield are shown in Table 2.

Example 13
Synthesis of (tetracarboxyphthalocyaninato)cobalt.

Into a 10000 ml four neck flask made of glass equipped with necessary equipment such as a stirrer, reflux condenser, and the like were charged 1152 g of trimellitic anhydride, 1800 g of urea, 10 g of ammonium molybdate, 360 g of cobalt chloride 6 hydrate and 3000 g of triglyme. The resulting mixture was stirred for 1 hour at temperature of 130° C., and subsequently stirred for 4 hours at temperature of 200° C.

The mixture was cooled to about 100° C., 5000 ml of hot water of about 80° C. was then gradually added to the reaction mixture, and further stirred for 2 to 3 hours with refluxing. After filtration at high temperature, the mixture was washed with 30 L of hot water. Then, the resulted wet cake was dropped into 6000 parts of 20 to 30% aqueous potassium hydroxide solution, and the mixture was stirred for 12 hours with refluxing. The reaction mixture was cooled using a water/ice bath, 4130 g of concentrated hydrochloric acid was added dropwise so that the temperature did not exceed 30° C., then the mixture was further stirred for one hour. The resulted slurry was filtered, and was desalted by washing with 80 to 100 L of water, then the product was dried to obtain 693.4 g of an intended compound at a yield of 61.9%. The result of the elemental analysis of this compound, the yield and molecule absorptivity coefficient $\epsilon$ are shown in Table 3.

Example 14
Synthesis of (tetracarboxyphthalocyaninato)iron(III).

Into a 5000 ml four neck flask made of glass equipped with necessary equipment such as a stirrer, reflux condenser, and the like were charged 384 g of trimellitic anhydride, 600 g of urea, 2 g of ammonium molybdate, 81 g of iron (III) chloride and 1500 g of tetraglyme. The resulting mixture was stirred for 1 hour at temperature of 130° C., and subsequently stirred for 6 hours at temperature of 180° C.

The mixture was cooled to about 100° C., 2500 g of hot water of about 80° C. was then gradually added to the reaction mixture, and further stirred for 2 to 3 hours with refluxing. After filtration at high temperature, the mixture was washed with 15 L of hot water. Then, the resulted wet cake was dropped into 3000 parts of 20 to 30% aqueous potassium hydroxide solution, and the mixture was stirred for 12 hours with refluxing.

The reaction mixture was cooled using a water/ice bath, 2065 g of concentrated hydrochloric acid was added dropwise so that the temperature did not exceed 30° C., then the mixture was further stirred for one hour. The resulted slurry was filtered, and was desalted by washing with 20 to 50 L of water, then the product was dried to obtain 265 g of an intended compound at a yield of 71.2%. The result of the elemental analysis of this compound and the yield are shown in Table 2.

Example 15
Synthesis of (octacarboxyphthalocyaninato)iron(III).

Into a 5000 ml four neck flask made of glass equipped with necessary equipment such as a stirrer, reflux condenser, and the like were charged 300 g of trimellitic dianhydride, 600 g of urea, 10 g of ammoniummolybdate, 100 g of iron (III) chloride and 1500 g of tetraglyme. The resulting mixture was stirred for 1 hour at temperature of 130° C., and subsequently stirred for 8 hours at temperature of 200° C.

The mixture was cooled to about 100° C., 2500 ml of hot water of about 80° C. was then gradually added to the reaction mixture, and further stirred for 2 to 3 hours with refluxing. After filtration at high temperature, the mixture was washed with 15 L of hot water. Then, the resulted wet cake was dropped into 3000 parts of 5 to 10% aqueous potassium hydroxide solution, and the mixture was stirred for 2 hours with refluxing.

The reaction mixture was cooled using a water/ice bath, 520 g of concentrated hydrochloric acid was added dropwise so that the temperature did not exceed 30° C., then the mixture was further stirred for one hour. The resulted slurry was filtered, and was desalted by washing with 20 to 50 L of water, then the product was dried to obtain 160 g of an intended compound at a yield of 51.0%. The result of the elemental analysis of this compound and the yield are shown in Table 2.

Example 16
Synthesis of cobaltphthalocyanine.

Into a 10 L four neck flask made of glass equipped with necessary equipment such as a stirrer, reflux condenser, and the like were charged 741 g of phthalic anhydride, 1500 g of urea, 10 g of ammonium molybdate, 328 g of cobalt chloride 6 hydrate and 3500 g of triglyme. The resulting mixture was stirred for 1 hour at temperature of 130° C., and subsequently stirred for 6 hours at temperature of 200° C.

The mixture was cooled to about 100° C., 4000 ml of hot water of about 80° C. was then gradually added to the reaction mixture, and further stirred for 2 to 3 hours with refluxing. After filtration at high temperature, the mixture was washed with 30 L of hot water. After drying, 636 g of an intended compound was obtained at a yield of 89.1%. The result of the elemental analysis of this compound and the yield are shown in Table 2.

The phthalocyanine producing material, metallizing agent and reaction solvent used in the above-described examples were substituted by the above-described phthalic acids or functional derivatives thereof and metallizing agents to synthesize various metallophthalocyanines. All results were excellent, and there could be synthesized metallophthalocyanines having high purity which require no pigmentation treatment directly (by one pot).

Comparative Example 4
Synthesis of (tetracarboxyphthalocyaninato)cobalt.

Into a 100 ml four neck flask made of glass equipped with necessary equipment such as a stirrer, reflux condenser, and the like were charged 3.84 g of trimellitic anhydride, 12.0 g of urea, 0.5 g of ammonium molybdate, 1.30 g of cobalt chloride 6 hydrate and 60 g of nitrobenzene, and a condensation reaction was conducted according to the Weilar method.

The nitrobenzene solvent was removed under reduced pressure from the reaction mixture, then, to this was added 100 ml of hot water, and the mixture was further stirred with heating. After filtration, the product was hydrolyzed with 60 ml of 20 to 30% aqueous potassium hydroxide solution, the mixture was filtered, washed with water and dried to obtain 3.65 g of an intended compound at a yield of 97.7%. The result of the elemental analysis of this compound, the yield and molecule absorptivity coefficient $\epsilon$ are shown in Table 2.

Comparative Example 5
Synthesis of (tetracarboxyphthalocyaninato)cobalt.

The same procedure as in Comparative Example 4 was conducted except that trichlorobenzene was used as a reaction solvent insteadof nitrobenzene to obtain 3.90 g of an intended compound at a yield of 104.4%. The result of the elemental analysis of this compound, the yield and molecule absorptivity coefficient $\epsilon$ are shown in Table 3.

Comparative Example 6
Synthesis of (tetracarboxyphthalocyaninato)cobalt.

The same procedure as in Example 13 was conducted except that diethylene glycol was used as a reaction solvent instead of triglyme to obtain no intended phthalocyanine.

Comparative Example 7
Synthesis of (tetracarboxyphthalocyaninato)iron(III).

The same procedure as in Example 14 was conducted except that ethylene glycol monoethyl ether (ethyl cellosolve) was used as a reaction solvent instead of tetraglyme to obtain no intended phthalocyanine.

TABLE 2

|  | Example 12 | | Example 14 | | Example 15 | | Example 16 | |
|---|---|---|---|---|---|---|---|---|
| Yield(%) | 93.6 | | 71.2 | | 51.0 | | 89.1 | |
| Element analys. | Calc. value | Found value | Calc. value | Found value | Calc. value | Found value | Calc. Value | Found value |
| C | 50.56 | 50.33 | 56.06 | 56.37 | 52.17 | 47.18 | 67.25 | 68.36 |
| H | 2.11 | 2.08 | 2.15 | 2.29 | 1.74 | 2.27 | 2.80 | 2.31 |
| N | 22.12 | 23.50 | 15.05 | 16.18 | 12.17 | 14.65 | 19.61 | 20.71 |
| Metal | 8.36 (Cu) | 8.42 | 7.53 (Fe) | 4.67 | 6.09 (Fe) | 4.47 | 10.3 (Co) | 7.90 |

TABLE 3

|  | Example 13 | | Comparative Example 4 | | Comparative Example 5 | |
|---|---|---|---|---|---|---|
| Yield(%) | 61.9 | | 97.9 | | 104.4 | |
| $\epsilon$ ($\lambda 1$) | 37500 | | 27500 | | 42500 | |
| $\epsilon$ ($\lambda 2$) | 47000 | | 37000 | | 33800 | |
| Element analys. | Calc. value | Found value | Calc. value | Found value | Calc. value | Found value |
| C | 57.83 | 57.40 | 57.83 | 53.23 | 57.83 | 53.03 |
| H | 2.14 | 2.08 | 2.14 | 1.31 | 2.14 | 0.81 |
| N | 14.99 | 14.36 | 14.99 | 15.36 | 14.99 | 15.13 |
| Metal | 7.90 (Co) | 7.82 | 7.90 (Co) | 7.69 | 7.90 (Co) | 7.08 |

In Examples 1 to 5 and 12 to 16, the reaction product from which a solvent had been removed after the condensation reaction was a uniform slurry. On the other hand, in Comparative Examples 4 and 5, the reaction product was set and adhered to the wall of a vessel, and partially became impossible to stir. In comparative examples, high yield was obtained, the reason for this is that the product contained a large amount of impurities which were by-produced by this reaction. This is evident from the molecule absorptivity coefficients and the results of elemental analysis as to Example 13 and Comparative Examples 4 and 5 shown in Table 3.

Figure 4:
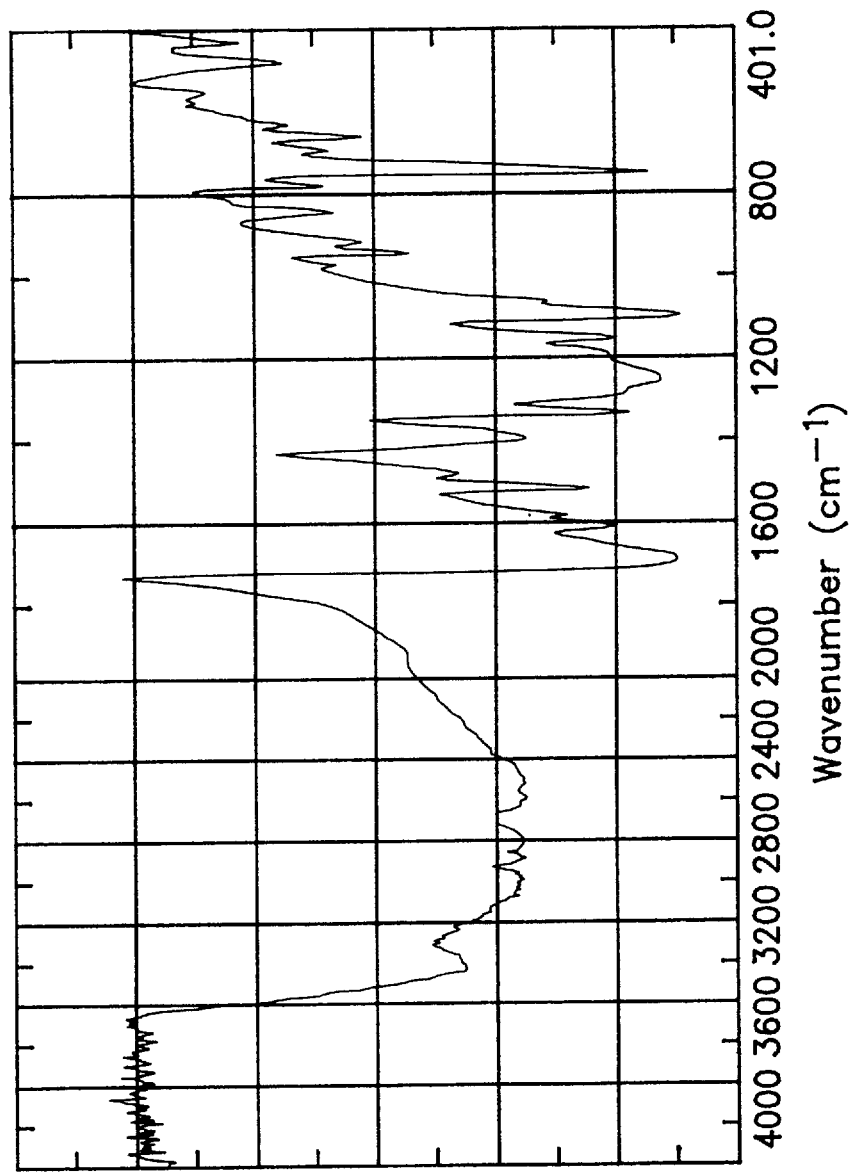
FIG. 4 is a graph which shows the IR spectrum of (tetracarboxyphthalocyaninato)cobalt obtained in Example 13.
Figure 5:
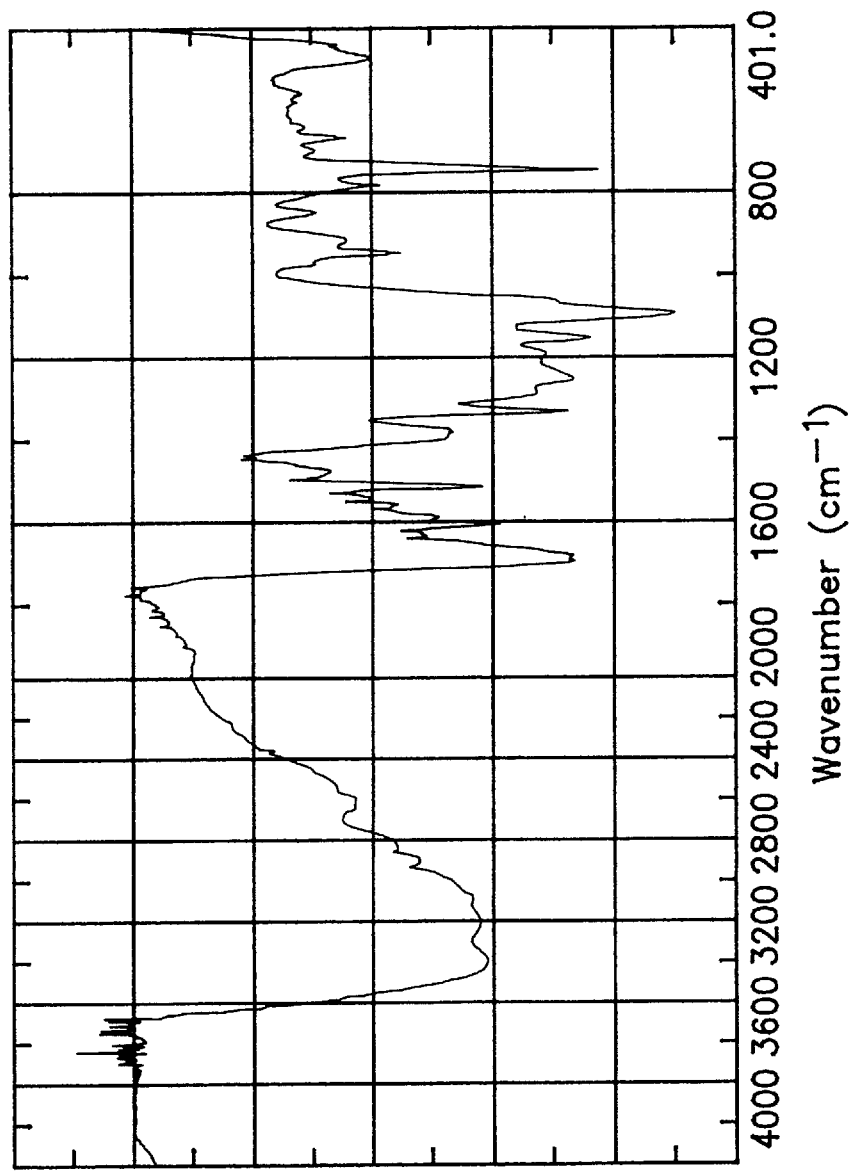
FIG. 5 is a graph which shows the IR spectrum of (tetracarboxyphthalocyaninato)cobalt obtained in Comparative Example 4.

Further, to investigate purity of the product, infrared absorption spectra of (tetracarboxyphthalocyaninato)cobalt in Example 13 and Comparative Example 4 are shown in FIGS. 4 and 5. Though both spectra have specific absorption derived from (tetracarboxyphthalocyaninato)cobalt, it is known from the spectra that a carbonyl absorption ($\upsilon_{c=o}$) appears at about 1700 cm$^{-1}$ at the same strength as the absorption derived from a phthalocyanine bone in Example 13, and on the other hand, in Comparative Example 4, the relative strength of the carbonyl absorption ($\upsilon_{c=o}$) is weak and the purity is low. The same results were also obtained as to Comparative Example 5.

What is claimed is:

1. A water-soluble metallophthalocyanine represented by the formula:

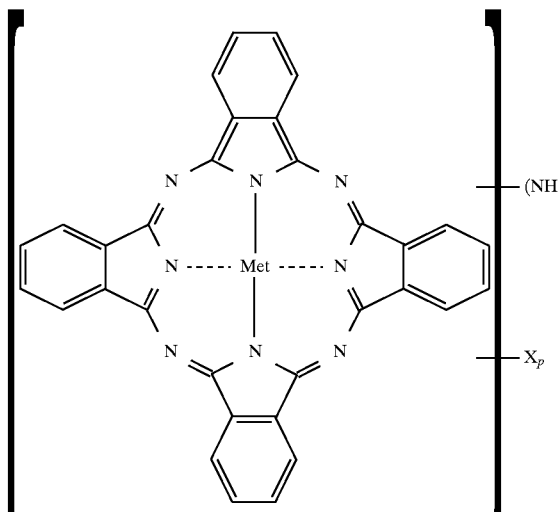

wherein, "Met" is a central metal, X is an acidic group or alkali metal salt thereof, m and p are respectively an integer of from 1 to 15, and m+p is not more than 16.

2. The water-soluble metallophthalocyanine according to claim 1, wherein X is a carboxyl group, a sulfonic acid group, or alkali metal salt thereof.

3. The water-soluble metallophthalocyanine according to claim 1, wherein m and p are independently an integer of 1 to 3, and m+p is an integer of not more than 4.

4. A material for deodorizing at least one odor selected from the group consisting of an aldehyde-origin odor, an amine-origin odor, and a sulfur-origin odor, which has a support, and the water-soluble metallophthalocyanine specified in claim 1 deposited thereon.

5. The material according to claim 4, wherein the support is a polymer powder or granules of a cellulose material, or a peracetic acid-treated wool material.

6. A process for deodorizing at least one odor selected from the group consisting of an aldehyde-origin odor, an amine-origin odor, and a sulfur-origin odor, which comprises the step of: placing the material specified in claim 4 at the location of the odor.

7. A process for preparing the water-soluble metallophthalocyanine specified in claim 1 which comprises the steps of:

heating a phthalic acid derivative having a nitro groups, a phthalic acid derivative having an acidic group, urea, and metal halide, in polyethylene glycol dialkyl ether, in the presence of a condensation catalyst to obtain a metallophthalocyanine having a nitro group and an acidic group; and reducing the metallophthalocyanine having a nitro group and an acidic group.

8. The process according to claim 7, wherein the phthalic acid derivative having a nitro group is selected from the group consisting of 3-nitrophthalic acid, 4-nitrophthalic acid, triammonium sulfophthalate, 3-nitrophthalic anhydride, 4-nitrophthalic anhydride, 3-nitrophthalimide, 4-nitrophthalimide, and 4-chloro-5-nitrophthalimide.

9. The process according to claim 7, wherein the phthalic acid derivative having an acidic group is selected from the group consisting of trimellitic anhydride, pyromellitic anhydride, 3-sulfophthalic anhydride, 4-sulfophthalic anhydride, trimellitic acid, pyromellitic acid, 3-sulfophthalic acid, 4-sulfophthalic acid, and Na, K, and NH$_3$ salts thereof, and amide derivatives thereof.

10. The process according to claim 7, wherein the polyethylene glycol dialkyl ether is polyglyme.

11. A material for deodorizing at least one odor selected from the group consisting of an aldehyde-selected from the group consisting of an aldehyde-origin odor, an amine-origin odor, and a sulfur origin odor, consisting of 10 to 90% by weight of a metallophthalocyanine which has 1 to 16 amino groups as a substituent, and a metallophthalocyanine which has 1 to 16 acidic groups or alkali metal salt thereof as a substituent.

12. A process for preparing a metallophthalocyanine compound, wherein polyethylene glycol dialkyl ether is used as a reaction solvent.

13. A process for preparing a metallophthalocyahine compound which comprises the step of: heating a phthalic acid derivative, urea, and metal halide, in polyethylene glycol dialkyl ether, in the presence of a condensation catalyst.

14. The process according to claim 13, wherein the phthalic acid derivative is at least one selected from the group consisting of phthalic anhydride, trimellitic anhydride, pyromellitic dianhydride, 4-sulfophthalic acid, alkyl-substituted phthalic acid, alkoxy-substituted phthalic acid, ammonium salt of phthalic acid, metal salt (Na salt, K salt) of phthalic acid, phthalate, phthalamide, phthalyl halogenate, phthalimide, o-cyanobenzoic acid, and o-cyanobenzoate.

15. The process according to claim 12 or 13, wherein the polyethylene glycol dialkyl ether is polyglyme.

* * * * *